(12) United States Patent
Vogt et al.

(10) Patent No.: US 11,751,921 B2
(45) Date of Patent: Sep. 12, 2023

(54) INTRAMEDULLARY NAIL FOR THE APPLICATION OF PHARMACEUTICAL FLUIDS

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 87 days.

(21) Appl. No.: 17/217,141

(22) Filed: Mar. 30, 2021

(65) Prior Publication Data

US 2021/0298801 A1   Sep. 30, 2021

(30) Foreign Application Priority Data

Mar. 31, 2020 (EP) ..................................... 20167055

(51) Int. Cl.
*A61B 17/72* (2006.01)
*A61B 17/00* (2006.01)
(Continued)

(52) U.S. Cl.
CPC .... *A61B 17/72* (2013.01); *A61B 2017/00477* (2013.01); *A61B 2017/561* (2013.01); *A61M 5/16881* (2013.01)

(58) Field of Classification Search
CPC ... A61B 17/72–7291; A61B 2017/561; A61M 5/16881
See application file for complete search history.

(56) References Cited

U.S. PATENT DOCUMENTS 5,618,286 A * 4/1997 Brinker ................. A61M 37/00
606/62
5,626,581 A * 5/1997 Staehlin ............. A61B 17/7216
606/53

(Continued)

FOREIGN PATENT DOCUMENTS

| CN | 2857862 Y | 1/2007 |
|---|---|---|
| CN | 201370624 Y | 12/2009 |
| EP | 2399533 A1 | 12/2011 |

OTHER PUBLICATIONS

Extended European Search Report dated Sep. 24, 2020 by the European Patent Office for priority European patent application No. 20167055.1 (with partial, machine generated English translation).

*Primary Examiner* — Eduardo C Robert
*Assistant Examiner* — Steven J Cotroneo
(74) *Attorney, Agent, or Firm* — Dicke, Billig & Czaja, PLLC

(57) ABSTRACT

The invention relates to an intramedullary nail for the application of a pharmaceutical fluid, comprising a fluid-conducting first conduit means, which runs axially in the intramedullary nail and which can be connected to a first reservoir for the pharmaceutical fluid, and at least one lead-through, which connects the first conduit means in a fluid-conducting manner to an outer surface of the intramedullary nail. The invention furthermore relates to a method for the treatment of bone fractures and for the application of a pharmaceutical fluid into the area of a bone canal by means of an intramedullary nail.

20 Claims, 7 Drawing Sheets

(51) Int. Cl.
  *A61B 17/56* (2006.01)
  *A61M 5/168* (2006.01)

(56) References Cited

U.S. PATENT DOCUMENTS

| | | | | |
|---|---|---|---|---|
| 5,681,289 | A * | 10/1997 | Wilcox | A61F 2/32 |
| | | | | 606/62 |
| 8,609,003 | B2 * | 12/2013 | Vaidya | A61B 17/8802 |
| | | | | 425/117 |
| 10,736,745 | B2 * | 8/2020 | Forsell | A61F 2/30721 |
| 10,744,313 | B2 * | 8/2020 | Williams | A61M 31/002 |
| 11,273,044 | B2 * | 3/2022 | Foran | A61M 39/0208 |
| 2016/0067138 | A1 * | 3/2016 | Johnson | A61M 37/00 |
| | | | | 601/148 |
| 2016/0367371 | A1 * | 12/2016 | de Beaubien | A61F 2/34 |
| 2019/0175232 | A1 * | 6/2019 | Karg | A61B 17/1725 |
| 2019/0290833 | A1 * | 9/2019 | Vogt | A61M 39/24 |
| 2021/0113251 | A1 * | 4/2021 | Vogt | A61M 5/16881 |
| 2021/0259748 | A1 * | 8/2021 | Mullaney | A61B 17/72 |
| 2022/0233763 | A1 * | 7/2022 | Zhang | A61M 5/1422 |

* cited by examiner

INTRAMEDULLARY NAIL FOR THE APPLICATION OF PHARMACEUTICAL FLUIDS

CROSS REFERENCE TO RELATED APPLICATIONS

This application claims priority to European Patent Application No. 20167055.1, filed on Mar. 31, 2020, the entire disclosure of which is incorporated by reference herein.

FIELD OF THE INVENTION

The invention relates to an intramedullary nail for the application of a pharmaceutical fluid, comprising a fluid-conducting first conduit means, which runs axially in the intramedullary nail and which can be connected to a first reservoir for the pharmaceutical fluid, and at least one lead-through, which connects the first conduit means in a fluid-conducting manner to an outer surface of the intramedullary nail.

The invention furthermore relates to a method for the treatment of bone fractures and for the application of a pharmaceutical fluid into the area of a bone canal by means of an intramedullary nail.

BACKGROUND OF THE INVENTION

The use of intramedullary nails has proven itself for decades for the surgical treatment of open as well as closed bone fractures, in particular for the treatment of bone fractures of large long bones. For this purpose, an intramedullary nail, which remains inside the bone canal at least until the bone fracture has healed, is inserted and fixed in the bone canal in order to reposition and stabilize the fractured bone.

Bone fractures, in particular open bone fractures, can result in contamination of the bone tissue with microorganisms. The infections caused in this way, such as, for example, an osteitis, in particular an osteomyelitis, represents extremely serious illnesses.

To treat the microbial infections, a topical application of antibiotics is common after a surgical debridement of the infected bone tissue.

Intramedullary nails, which are covered with PMMA bone cement containing one or several antibiotics, are described in U.S. Pat. No. 8,609,003 B2 and in U.S. Pat. No. 5,618,286 A. It turns out to be disadvantageous thereby that the antibiotics incorporated in the PMMA bone cement can release a sufficiently high concentration of antibiotics only within the first few days after the implantation of the intramedullary nail, which can be too short for a final combatting of the infection. The antibiotic composition can furthermore not be varied after implantation has occurred, which is disadvantageous in particular in the case of an inefficacy of the antibiotics contained in the PMMA bone cement.

Intramedullary nails comprising a perforated intramedullary nail bodies, by means of which different pharmaceutical fluids, such as, for example, antiseptic active substance solutions, can be applied topically at the infected bone tissue via supply from the outside, thus represent a further development. Intramedullary nails of this type are described, for example, in U.S. Pat. No. 5,681,289 A, in CN 2857862 Y and in CN 201370624 Y. An antiseptic active substance solution can thereby escape through lead-throughs in the corresponding intramedullary nails and can reach the infected bone tissue.

One disadvantage of the described intramedullary nails is an unwanted accumulation of the active substance contained in the pharmaceutical fluid in the patient body, which is caused by the high application pressure required when pressing the fluid into the bone canal. In the case of a number of antibiotics, such as, for example, aminoglycoside antibiotics, high systemic antibiotic concentrations can cause damages to the patient, such as, for example, kidney damages and damages to the auditory nerve. The pressure build-up caused by the application furthermore increases the risk of emboli. In addition, an uncontrolled backward flow of the pharmaceutical fluid through the access previously used for the introduction can occur, and the contamination of the rinsing system, in particular of the intramedullary nail, can thus occur.

SUMMARY OF THE INVENTION

It is an object of the present invention to at least partially overcome one or several of the disadvantages resulting from the prior art.

In particular, the invention is based on the goal of providing intramedullary nails, which are able to rinse the interior space of bones, in particular of long bones, with pharmaceutical fluids of any composition, in particular with antiseptic active substance solutions, such as, for example, active substance solutions containing antibiotics. The pharmaceutical fluid is to thereby be capable of being supplied to the intramedullary nail from a reservoir arranged outside of the patient body, and side effects, such as, for example, the accumulation of the supplied active substance in the patient body and the formation of emboli, in particular of fat emboli, is to be avoided. It is additionally the goal to reliably distribute the active substance solution over the interior space of the bones, and to simultaneously ensure a high mechanical stability of the intramedullary nails, and a secure fixation of the latter in the bone. In addition, the intramedullary nails are to provide for a safe and controllable rinsing of an interior space of a bone, without thereby resulting in a contamination or a clogging of the intramedullary nails, in particular by the ingress of bone tissue into the intramedullary nails.

A contribution to at least partially fulfilling at least one of the above-mentioned objects is made by the features of the independent claims. The dependent claims provide preferred embodiments, which contribute to at least partially fulfilling at least one of the objects.

|1| An intramedullary nail for the application of a pharmaceutical fluid, comprising a fluid-conducting first conduit means, which runs axially in the intramedullary nail and which can be connected to a first reservoir for the pharmaceutical fluid, and at least one lead-through, which connects the first conduit means in a fluid-conducting manner to an outer surface of the intramedullary nail, characterized in that a fluid-conducting second conduit means connects the outer surface to a second reservoir so as to convey the pharmaceutical fluid between the first reservoir and the second reservoir.

|2| The intramedullary nail according to embodiment 1, characterized in that the first conduit means comprises a first connector for the fluid-conducting connection to the first reservoir, and the second conduit means comprises a second connector for the fluid-conducting connection to the second reservoir, wherein the first connector and the second connector are arranged at a first end of the intramedullary nail.

[3] The intramedullary nail according to embodiment 2, characterized in that the at least one lead-through is arranged at a second end of the intramedullary nail opposite to the first end.

[4] The intramedullary nail according to any one of the preceding embodiments, characterized in that the second conduit means is at least partially formed as at least one axially extending groove in the outer surface.

[5] The intramedullary nail according to embodiment 4, characterized in that the at least one axially extending groove is connected in a fluid-conducting manner to the at least one lead-through.

[6] The intramedullary nail according to embodiment 4 or 5, characterized in that the second conduit means is formed as two to six, in particular as four axially extending grooves in the outer surface, and the intramedullary nail has the same number of lead-throughs, wherein one groove is in each case interconnected in a fluid-conducting manner to a respective lead-through.

[7] The intramedullary nail according to any one of the preceding embodiments, characterized in that the first conduit means has a first non-return valve.

[8] The intramedullary nail according to embodiment 7, characterized in that the first non-return valve is embodied so as to be fluid-permeable in the direction of the at least one lead-through.

[9] The intramedullary nail according to embodiment 7 or 8, characterized in that the first non-return valve has a first restoring element, in particular a first spring.

[10] The intramedullary nail according to any one of the preceding embodiments, characterized in that the second conduit means has a second non-return valve.

[11] The intramedullary nail according to embodiment 10, characterized in that the second non-return valve is embodied so as to be fluid-impermeable in the direction of the outer surface.

[12] The intramedullary nail according to embodiment 10 or 11, characterized in that the second non-return valve has a second restoring element, in particular a second spring.

[13] The intramedullary nail according to any one of the preceding embodiments, characterized in that the intramedullary nail has at least one bore in order to fix the intramedullary nail inside a bone canal.

[14] A method for the treatment of bone fractures and for the application of a pharmaceutical fluid into the area of the bone canal by means of an intramedullary nail comprising a fluid-conducting first conduit means, which runs axially in the intramedullary nail and which can be connected to a first reservoir for the pharmaceutical fluid, at least one lead-through, which connects the first conduit means in a fluid-conducting manner to an outer surface of the intramedullary nail, wherein the outer surface can be connected via a fluid-conducting second conduit means to a second reservoir for the pharmaceutical fluid, at least comprising the steps of a) implanting the intramedullary nail into the bone canal; b) fluid-conducting connection of the first conduit means to the first reservoir and of the second conduit means to the second reservoir; c1) at least partial conveying of the pharmaceutical fluid out of the first reservoir via the first conduit means, the at least one lead-through, the outer surface, and the second conduit means into the second reservoir; and/or c2) at least partial conveying of the pharmaceutical fluid out of the second reservoir via the second conduit means, the outer surface, the at least one lead-through, and the first conduit means into the first reservoir.

[15] The method according to embodiment 14, characterized in that the method comprises the steps a), b), and c1).

DETAILED DESCRIPTION OF EMBODIMENTS

Figure 1:
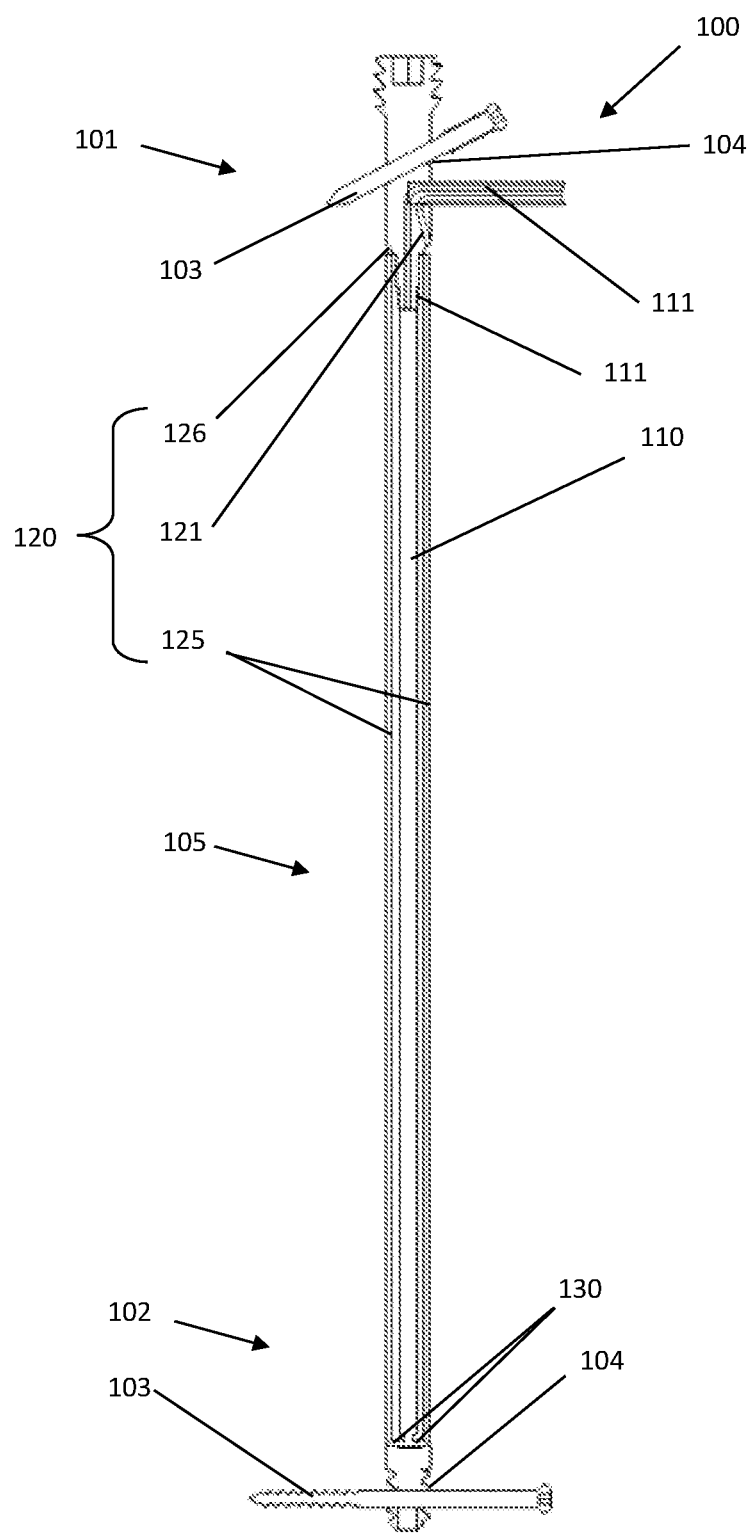
FIG. 1 shows a schematic cross-section of an intramedullary nail.

In the present description, range specifications also include the values mentioned as limits. A designation of the type "in the range of X to Y" with regard to a variable A thus means that A can take on the values X, Y and values between X and Y. Ranges of the type "up to Y", which are limited on one side, for a variable A, accordingly mean Y and less than Y as value.

Some of the described features are linked with the term "essentially". The term "essentially" is to be understood such that under actual conditions and production techniques, a mathematically exact interpretation of concepts, such as "overlap", "perpendicular", "diameter", or "parallelism" can never be specified exactly, but only within certain production-related error tolerances. For example, "essentially parallel axes" draw an angle of 85 degrees to 95 degrees relative to one another, and "essentially identical volumes" comprise a deviation of up to 5% by volume. A "device consisting essentially of plastic" comprises a plastic content of, for example, ≥95 to ≤100% by weight. An "essentially complete filling of a volume B" comprises a filling of, for example, ≥95 to ≤100% by volume of the total volume of B.

A first subject matter of the invention relates to an intramedullary nail for the application of a pharmaceutical fluid, comprising a fluid-conducting first conduit means, which runs axially in the intramedullary nail and which can be connected to a first reservoir for the pharmaceutical fluid, and at least one lead-through, which connects the first conduit means in a fluid-conducting manner to an outer surface of the intramedullary nail, characterized in that a fluid-conducting second conduit means connects the outer surface to a second reservoir so as to convey the pharmaceutical fluid between the first reservoir and the second reservoir.

An intramedullary nail represents an intramedullary splinting when treating a bone fracture, in particular of a long bone, which stabilizes the bone until the bone fracture is healed. Drilled-out and non-drilled-out intramedullary nails are used primarily in practice, whereby the terms "drilled-out" and "non-drilled-out" refer to the implantation method of the intramedullary nails. In the case of drilled-out intramedullary nails, the entire medullary cavity of the long bone is drilled out, and the intramedullary nail is subsequently driven into the drilled-out bone canal. A mechanical locking in order to fix the intramedullary nail inside the bone canal is not obligatory.

Non-drilled-out intramedullary nails are more massive, but thinner than drilled-out intramedullary nails, wherein a fixation by means of locking screws is generally required. The intramedullary nail according to the invention can be used as drilled-out intramedullary nail, but also as non-drilled-out intramedullary nail, whereby the use as drilled-out intramedullary nail is preferred.

The intramedullary nail according to the invention serves for the application of a pharmaceutical fluid for the treatment of infected bone tissue, in particular for the application inside the bone canal of the bone, for a time period of several days to weeks. A pharmaceutical fluid contains at least one pharmaceutical active substance. The pharmaceutical fluid is, for example, aqueous or non-aqueous solutions or suspensions of pharmaceutical active substances.

In one embodiment, the pharmaceutical fluid is solutions, which contain at least one antibiotic, at least one chemotherapeutic agent, and/or at least one antifungal agent. In a further embodiment, the pharmaceutical fluids contain at least one disinfectant component.

Pharmaceutical fluids furthermore also comprise gases, gas mixtures, and solutions of gases in liquids, such as, for example, water.

The intramedullary nail has a first conduit means and a second conduit means. A conduit means is understood to be all elements, which can connect two structures to one another in a fluid-conducting manner. Pipe-like, hose-like, or lead-through-like connections are examples for such elements.

To ensure a sufficiently high flow rate for the application of the pharmaceutical fluid, the first conduit means and/or the second conduit means can have an inner cross-section of, for example, between 0.5 mm$^2$ and 5 mm$^2$, preferably of between 1 mm$^2$ and 4 mm$^2$. To prevent a conveying of solids, and thus a risk of a clogging of the first conduit means and/or of the second conduit means, the first conduit means and/or the second conduit means can each have a screen or consist of a screen.

The first conduit means runs at least partially axially inside the intramedullary nail. The axial course of the first conduit means inside the intramedullary nail can be embodied in different ways. Due to the simple production method, the first conduit means preferably runs at least partially parallel to the longitudinal axis of the intramedullary nail.

The distance, over which the first conduit means runs axially inside the intramedullary nail, can be embodied to be of different lengths. For example, the first conduit means can run axially through 1-100% of a total length of the intramedullary nail. The first conduit means can pass axially through, for example, at least 1%, 10%, 70%, 80% of the total length of the intramedullary nail. As upper limit, the first conduit means can axially pass through maximally 100%, 95%, 90%, or 85% of the total length of the intramedullary nail.

The intramedullary nail can be connected in a fluid-conducting manner to a first reservoir via the first conduit means and to a second reservoir for a pharmaceutical fluid via the second conduit means. A reservoir is understood to be all containers, which are suitable to provide and/or accommodate the pharmaceutical fluid. Examples for reservoirs include bags, syringes, plungers, balloons, canisters, and ampules, whereby bags, balloons, and syringes are preferred. A reservoir for accommodating the pharmaceutical fluid can furthermore be a bag, a vessel, or a different type of collection container, which does not need to be structurally connected to the first conduit means or to the second conduit means, but which is suitable to collect the pharmaceutical fluid escaping out of the first conduit means or the second conduit means. In one embodiment, the reservoir accommodating the pharmaceutical fluid can also be a room or a floor of a room, into which the pharmaceutical fluid, which escapes out of the first conduit means or the second conduit means, is discharged, or onto which the fluid, which is liquid in this case, flows or drips.

The first conduit means is connected in a fluid-conducting manner to an outer surface of the intramedullary nail via at least one lead-through, wherein the outer surface represents the surface area of the intramedullary nail, which is in physical contact with the bone tissue of the patient. In one embodiment, the at least one lead-through is embodied as at least one perforation in the intramedullary nail, which connects the first conduit means in a fluid-conducting manner to the outer surface. To ensure a sufficiently high flow rate through the at least one lead-through for the application of the pharmaceutical fluid, the lead-through can have an inner cross-section of between 0.5 mm$^2$ and 5 mm$^2$, preferably between 1 mm$^2$ and 4 mm$^2$. To prevent a conveying of solids, and thus a risk of a clogging of the lead-through, the at least one lead-through can have a screen, can consist of a screen, or can have a closure, such as, for example, a flap, which opens only in response to the conveying of the pharmaceutical fluid through the at least one lead-through, but which remains closed otherwise, and thus prevents an ingrowth of tissue, and thus a clogging of the at least one lead-through.

The first reservoir can be connected in a fluid-conducting manner to the second reservoir via the first conduit means, the at least one lead-through, the outer surface of the intramedullary nail, and the second conduit means, in order to convey the pharmaceutical fluid between the first reservoir and the second reservoir, so that the pharmaceutical fluid can be applied to the infected bone tissue surrounding the intramedullary nail.

In one embodiment, the pharmaceutical fluid can be conveyed out of the first reservoir into the second reservoir via the first conduit means, the at least one lead-through, the outer surface of the intramedullary nail, and the second conduit means. In a further embodiment, the pharmaceutical fluid can be conveyed out of the second reservoir into the first reservoir via the second conduit means, the outer surface of the intramedullary nail, the at least one lead-through, and the first conduit means.

In both embodiments, the pharmaceutical fluid comes into contact with the bone tissue of the patient via the outer surface of the intramedullary nail, and thus allows an application of the active substance contained in the pharmaceutical fluid to fight infections in the area of the bone fracture. The pharmaceutical fluid simultaneously does not remain in the area of the infected bone tissue, but can be discharged into the first reservoir or the second reservoir. A continued supply of the pharmaceutical fluid thus does not create a pressure build-up due to fluid, which remains in the bone canal, whereby an unwanted increased introduction of the active substance into the bloodstream of the patient is prevented. This prevents an accumulation of the active substance in the patient and additionally reduces the risk of emboli.

One embodiment of the intramedullary nail is characterized in that the first conduit means comprises a first connector for the fluid-conducting connection to the first reservoir, and the second conduit means comprises a second connector for the fluid-conducting connection to the second reservoir, wherein the first connector and the second connector are arranged at a first end of the intramedullary nail.

A connector is understood to be a structural unit, which allows a fluid-conducting connecting of conduit means and reservoir. In one embodiment, the connector is formed as grommet, via which the conduit means can be connected in a fluid-conducting manner to the reservoir by means of a hose. In a further embodiment, the connector is formed as thread, which can be connected in a fluid-conducting manner to the reservoir via a corresponding counter piece. In a further embodiment, the connector forms a flange connection with the reservoir. In a further embodiment, the connector forms a fluid-conducting connection with the reservoir via a hose coupling, wherein the connector can have the coupling or the nipple of the hose coupling.

The first connector and the second connector are arranged together at a first end of the intramedullary nail, so that the supply and discharge of the pharmaceutical fluid into or out of the bone canal, respectively, can take place at the same end of the bone. The first connector and the second connector is preferably located at the end of the intramedullary nail, which faces the opening of the bone designated for the implantation of the intramedullary nail. In a preferred embodiment, the first connector and the second connector form a common structural element, such as, for example, a common grommet, which allows the use of a twin hose system for supplying and discharging the pharmaceutical fluid into or out of the intramedullary nail, respectively.

One embodiment of the intramedullary nail is characterized in that the at least one lead-through is arranged at a second end of the intramedullary nail opposite to the first end. The first conduit means thus extends from the first end of the intramedullary nail, where the first connector is located, to the second end of the intramedullary nail, at which the lead-through connects the first conduit means in a fluid-conducting manner to the outer surface of the intramedullary nail. The first conduit means preferably extends axially over 70-100%, more preferably over 80-100%, even more preferably over 85-95% of the total length of the intramedullary nail.

In a preferred embodiment, the second conduit means is embodied in such a way, for example as at least one canal into the intramedullary nail, that a discharging of the pharmaceutical fluid takes place from the outer surface of the intramedullary nail at the first end of the intramedullary nail. The pharmaceutical fluid is preferably guided at least over 60-100%, preferably 70-100%, more preferably between 80-95% of the total length of the intramedullary nail along the outer surface, starting with the at least one lead-through, before it is conveyed from the outer surface by means of the discharging design of the second conduit means. This ensures that the pharmaceutical fluid is guided along the outer surface over a majority of the total length of the intramedullary nail, while a conveying is performed between the first reservoir and the second reservoir. The intramedullary nail thus allows a treatment of infected bone tissue over a large area.

The pharmaceutical fluid can be guided along the outer surface of the intramedullary nail in different ways.

One embodiment of the intramedullary nail is characterized in that the second conduit means is at least partially formed as at least one axially extending groove in the outer surface. Due to the at least one groove, the pharmaceutical fluid can be conveyed safely, in larger quantities, and without the risk of a clogging, wherein a wetting for the outer surface along the groove ensures an effective fight of an infection. A pressure build-up due to continued conveying of the pharmaceutical fluid between the first reservoir and the second reservoir thus does not occur, which prevents an unwanted accumulation of the active substance contained in the pharmaceutical fluid, and reduces the risk of emboli. The second conduit means is preferably formed as several, for example as two to ten, axially running grooves, which are radially distributed over the outer surface of the intramedullary nail.

This allows an application of the pharmaceutical fluid over a large area in the entire area of the intramedullary nail with simultaneously reduced risk of an unwanted pressure build-up during the conveying.

The at least one axially extending groove can be embodied differently. In one embodiment, the at least one axially extending groove runs in wave-like deflections along the outer surface. In a further embodiment, the at least one groove runs helically along the outer surface. Due to the simpler production, the at least one axially extending groove runs essentially parallel to the longitudinal axis of the intramedullary nail.

The at least one groove can extend at different lengths along the longitudinal axis of the intramedullary nail. The at least one groove can extend along the outer surface, for example, over 5-100%, preferably over 50-100%, more preferably over 70-95% of the total length.

The at least one lead-through and the second conduit means can be connected to one another in a fluid-conducting manner in different ways. In one embodiment, the at least one lead-through and the second conduit means, in particular in the form of at least one groove, which extends axially in the outer surface, are not connected directly to one another in a fluid-conducting manner, but only via the outer surface of the intramedullary nail.

One embodiment of the intramedullary nail is characterized in that the at least one axially extending groove is connected directly in a fluid-conducting manner to the at least one lead-through, without the need for the pharmaceutical fluid to thereby be conveyed over the outer surface of the intramedullary nail. The risk of an unwanted pressure build-up when conveying the pharmaceutical fluid between the first reservoir and the second reservoir is thus further lowered.

One embodiment of the intramedullary nail is characterized in that the second conduit means is formed as two to six, in particular as four axially extending grooves in the outer surface, and the intramedullary nail has the same number of lead-throughs, wherein one groove is in each case interconnected directly in a fluid-conducting manner to a respective lead-through.

In one embodiment, the intramedullary nail allows a conveying of the pharmaceutical fluid out of the first reservoir into the second reservoir as well as out of the second reservoir into the first reservoir.

In order to allow a conveying of the pharmaceutical fluid in only one direction of flow, thus out of the first reservoir into the second reservoir or out of the second reservoir into the first reservoir, one embodiment of the intramedullary nail is characterized in that the first conduit means has a first non-return valve. It can be controlled in this way, which parts of the intramedullary nail are contaminated with pharmaceutical fluid, which has already come into contact with bone tissue. In addition, this allows selecting the direction of flow of the pharmaceutical fluid through the intramedullary nail, which is associated with the lower risk of a clogging.

One embodiment of the intramedullary nail is characterized in that the first non-return valve is embodied so as to be fluid-permeable in the direction of the at least one lead-through and so as to be fluid-impermeable in the direction of the first connector. The intramedullary nail thus only allows a conveying of the pharmaceutical fluid out of the first reservoir into the second reservoir. One advantage of this embodiment is that only unused pharmaceutical fluid can be conveyed through the first conduit means, which runs at least partially axially in the intramedullary nail, and a contamination and/or clogging of the first conduit means with bone tissue, which can accumulate in the pharmaceutical fluid after the contact with bone tissue, is made impossible.

Due to the fact that in a preferred embodiment of the intramedullary nail the pharmaceutical fluid can be supplied to the intramedullary nail through the first connector at the first end, and leaves again at the second end through the at least one lead-through, and the second conduit means simultaneously discharges the pharmaceutical fluid at the first end from the outer surface of the intramedullary nail as well as leaves the intramedullary nail through the second connector at the first end, the one conduit means of the two, which runs longer in the intramedullary nail interior, is protected against contamination and/or clogging by bone tissue, in particular by bone marrow, by means of the first non-return valve.

The first non-return valve can have different designs. In one embodiment, the first non-return valve comprises a non-return flap, which allows a conveying of the pharmaceutical fluid through the first conduit means only in one direction of flow, and closes the conduit means in a fluid-conducting manner in the opposite direction of flow.

One embodiment of the intramedullary nail is characterized in that the first non-return valve has a first restoring element, which closes the first non-return valve in a fluid-conducting manner in one direction, and allows a conveying of the pharmaceutical fluid through the first non-return valve in the opposite direction. Due to the simple construction and the safe usability, the restoring element preferably has a spring, in particular a helical spring, for example made of a plastic or of a metal, or the first restoring element consists of a spring, in particular a helical spring, for example made of a plastic or of a metal.

In one embodiment, the first non-return valve is formed as non-return ball valve. Due to the high structural robustness, the first non-return valve is formed as non-return poppet valve in a further, preferred embodiment.

The first restoring element can be arranged at different points inside the first conduit means, in order to allow a conveying of the pharmaceutical fluid in only one direction of flow.

To prevent a contamination and/or a clogging of the first conduit means as effectively as possible, a preferred embodiment of the intramedullary nail is characterized in that the first restoring element is arranged at the second end of the intramedullary nail. More preferably, the first restoring element is arranged at the point of the first conduit means, which is axially farthest away from the first end of the intramedullary nail, in particular at the transition from the first conduit means into the at least one lead-through.

To allow a conveying of the pharmaceutical fluid only in one direction of flow, thus out of the first reservoir into the second reservoir or out of the second reservoir into the first reservoir, one embodiment of the intramedullary nail is characterized in that the second conduit means has a second non-return valve.

One embodiment of the intramedullary nail is characterized in that the second non-return valve is embodied so as to be fluid-impermeable in the direction of the outer surface, and fluid-permeable in the direction of the second connector. The intramedullary nail thus allows a conveying of the pharmaceutical fluid only out of the first reservoir into the second reservoir. It is an advantage of this embodiment that only pharmaceutical fluid, which has not come into contact with bone tissue, can still be conveyed through the first conduit means, which runs at least partially in the intramedullary nail, and a contamination and/or a clogging of the first conduit means in the bone tissue, which can accumulate in the pharmaceutical fluid after the rinsing of the bone canal, is made impossible.

The second non-return valve can have different designs. In one embodiment, the second non-return valve comprises a non-return flap, which allows a conveying of the pharmaceutical fluid through the second conduit means only in one direction of flow, and closes the second conduit means in a fluid-conducting manner in the opposite direction of flow.

One embodiment of the intramedullary nail is characterized in that the second non-return valve has a second restoring element, which closes the second non-return valve in a fluid-conducting manner in one direction of flow, and allows a conveying of the pharmaceutical fluid through the second non-return valve in the opposite direction. Due to the simple construction and the safe usability, the second restoring element preferably has a spring, in particular a helical spring, for example made of a plastic or of a metal, or the second restoring element consists of a spring, in particular a helical spring, for example made of a plastic or of a metal.

In one embodiment, the second non-return valve is formed as non-return ball valve. Due to the high structural robustness, the second non-return valve is formed as non-return poppet valve in a further, preferred embodiment.

One embodiment of the intramedullary nail is characterized in that the intramedullary nail has at least one bore in order to fix the intramedullary nail inside a bone canal. For this purpose, a fastening means, such as, for example, a screw, can in each case be driven through the at least one bore as well as through the bone tissue surrounding the intramedullary nail, wherein a displacement and/or rotation of the intramedullary nail inside the bone canal is prevented. The intramedullary nail preferably has the at least one bore at the first end or at the second end of the intramedullary nail. More preferably, the intramedullary nail has at least one bore at the first end and at least one bore at the second end.

One embodiment of the intramedullary nail is characterized in that the intramedullary nail has at least one sealing ring. The at least one sealing ring surrounds the outer surface of the intramedullary nail in a fluid-impermeable manner and cooperates with the bone tissue surrounding the intramedullary nail in such a way after an implantation of the intramedullary nail that a pharmaceutical fluid, in particular a liquid pharmaceutical fluid, cannot be conveyed between sealing ring and bone tissue. Examples for sealing rings include foam rings made of a foamed plastic, or massive, non-foamed elastic plastic rings, in particular sealing rings made of elastomers. In one embodiment the intramedullary nail has at least one sealing ring at the first end. In a further embodiment, the intramedullary nail has at least one sealing ring at the second end. In a further preferred embodiment, the intramedullary nail has at least one sealing ring at the first end and at least one sealing at the second end. The at least one sealing ring at the first end and the at least one sealing ring at the second end encompass at least the second conduit means running at the outer surface in such a way that the pharmaceutical fluid can be conveyed in a controlled manner from the one reservoir into the other reservoir, but simultaneously prevent an unwanted distribution of the pharmaceutical fluid in the direction of and beyond the two axial ends of the intramedullary nail. This prevents an unwanted accumulation of the active substance contained in the pharmaceutical fluid in the patient.

A further object of the invention relates to a method for the treatment of bone fractures and for the application of a pharmaceutical fluid into the area of the bone canal by means of an intramedullary nail, in particular an intramedullary nail according to any one of the preceding embodiments. The method comprises at least the following steps:

a) implanting the intramedullary nail into the bone canal;
b) fluid-conducting connection of the first conduit means to the first reservoir and of the second conduit means to the second reservoir;
c1) at least partial conveying of the pharmaceutical fluid out of the first reservoir via the first conduit means, the at least one lead-through, the outer surface, and the second conduit means into the second reservoir; and/or
c2) at least partial conveying of the pharmaceutical fluid out of the second reservoir via the second conduit means, the outer surface, the at least one lead-through, and the first conduit means into the first reservoir.

In one embodiment of the method, steps c1) as well as c2) are performed, so that the pharmaceutical fluid is moved at least partially alternately between the first reservoir and the second reservoir.

In a further, preferred, embodiment of the method, either step c1) or step c2) is performed, so that the pharmaceutical fluid is conveyed only once in a direction of flow through the intramedullary nail. This prevents a contamination and/or a clogging of the intramedullary nail by bone tissue, in particular by bone marrow.

If the method comprises only step c1) or step c2), thus if the pharmaceutical fluid is conveyed only once through the intramedullary nail, the first reservoir or second reservoir accommodating the pharmaceutical fluid can be connected in a fluid-conducting manner to the first conduit means or to the second conduit means, respectively, in different ways in step b). In one embodiment, the reservoir accommodating the pharmaceutical fluid is directly physically connected to the corresponding conduit means, for example via a hose. In a further embodiment, the reservoir accommodating the pharmaceutical fluid, for example a bowl or a vessel, is not directly physically connected to the corresponding conduit means, but the corresponding reservoir only catches the pharmaceutical fluid escaping from the corresponding conduit means, for example as drops.

In a preferred embodiment of the method, the method comprises step c1) and not step c2). The first conduit means, which, compared to the second conduit means extends over a longer distance inside the intramedullary nail, is protected against contamination and clogging in a preferred embodiment.

The application of the pharmaceutical fluid can take place in different ways. In one embodiment, the pharmaceutical fluid is applied via the intramedullary nail into the bone canal, where it remains in the area of the bone canal for a time period of minutes to days, for example up to 10 days. In a further embodiment, the pharmaceutical fluid is conveyed through the intramedullary nail continuously once or several times, without time delay, so that the bone canal is rinsed once or several times with the pharmaceutical fluid.

The features disclosed for the intramedullary nail are also disclosed for the method and vice versa. A description of embodiments follows with specific reference to the Figures.

FIG. 1 shows a schematic cross-section of an intramedullary nail 100. The intramedullary nail 100 has an axially running first conduit means 110. The first conduit means 110 runs axially from a first end 101 to a second end 102 of the intramedullary nail 100. At the first end 101, the first conduit means 110 has a first connector 111, via which the intramedullary nail 100, in particular the first conduit means 110, can be connected in a fluid-conducting manner to a first reservoir for a pharmaceutical fluid. The first conduit means 110 is partially formed as axially running canal inside the intramedullary nail 100, through which a pharmaceutical fluid, in particular a liquid pharmaceutical fluid, can be conveyed. At the second end 102, the intramedullary nail 100 has lead-throughs 130, which connect the first conduit means 110 in a fluid-conducting manner to a second conduit means 120 and via the second conduit means 120 also to an outer surface 105 of the intramedullary nail 100. The shown intramedullary nail 100 has four lead-throughs (wherein one lead-through 130 is directed out of the drawing plane, and a further lead-through 130 is directed behind the drawing plane, and is thus not visible), which are each arranged at the intramedullary nail 100 radially offset from one another at an angle of 90°. In further, non-illustrated, embodiments of the intramedullary nail 100, the number as well as the arrangement of the lead-throughs 130 can vary.

In the shown embodiment, the second conduit means 120 comprises four grooves 125 running axially in the outer surface 105 (wherein again one of the axial grooves 125 runs in front of the drawing plane, and one further groove 125 runs behind the drawing plane, analogously to the lead-throughs 130), which connect directly to the four lead-throughs 130, a radially circumferential depression 126, as well as a canal-like second connector 121 at the first end 101 of the intramedullary nail 100, whereby the canal-like depression 126 connects the second connector 121 and the grooves 125 in a fluid-conducting manner.

In the shown embodiment of the intramedullary nail 100, the first connector 111 and the second connector 121 are formed in one piece in such a way that a first reservoir and a second reservoir can be connected to the intramedullary nail 100 by means of a twin hose system. In further, non-illustrated embodiments, the first connector 111 and the second connector 121 can be embodied separately from one another, so that a first reservoir and a second reservoir can in each case be connected to the first connector 111 and the second connector 121 by means of a separate connection means, such as, for example, a hose. In the shown embodiment, the first end 101 is fastened to the remainder of the intramedullary nail 100 by means of a screw connection 107. In further, non-illustrated embodiments, the first end 101 and the remainder of the intramedullary nail 100 is embodied in one piece.

The intramedullary nail 100 allows a conveying of a pharmaceutical fluid in two directions of flow. In a first embodiment, the pharmaceutical fluid can be introduced into the intramedullary nail 100 via the first connector 111 into the conduit means 110 and can be conveyed through the first conduit means 110 in the direction of the second end 102, wherein it is guided through the lead-throughs 130 out of the intramedullary nail 100 into the grooves 125 when reaching the second end 102. The grooves 125 guide the pharmaceutical fluid back in the direction of the first end 101 again, where it is collected by means of the radially circumferential depression 126 and is guided into a second reservoir by means of the second connector 121. In a further embodiment, the pharmaceutical fluid can be introduced into the intramedullary nail 100 out of a second reservoir via the second connector 121 into the second conduit means 120 and can be conveyed in the direction of the second end 102, wherein it is first guided through the radially circumferential depression 126 and subsequently via the grooves 125. When reaching the second end 102, the pharmaceutical fluid is introduced out of the grooves 125 through the lead-throughs 130 into the first conduit means 110. The first conduit means 110 guides the pharmaceutical fluid back in the direction of the first end 101 again, wherein it is transferred out of the intramedullary nail 100 into a first reservoir by means of the first connector 111 when reaching the first end 101.

In both embodiments, the pharmaceutical fluid is in fluid-conducting contact with the outer surface 105 of the intramedullary nail 100 via the grooves 125, which allows an application of the active substance contained in the pharmaceutical fluid to the surrounding bone tissue of the implanted intramedullary nail 100.

Bores 104, which are each provided with a fastening means 103 in the form of a screw, are attached at the first end 101 and at the second end 102. The fastening means 103 serve the purpose of spatially fixing the intramedullary nail 100 inside a bone canal.

Figure 2:
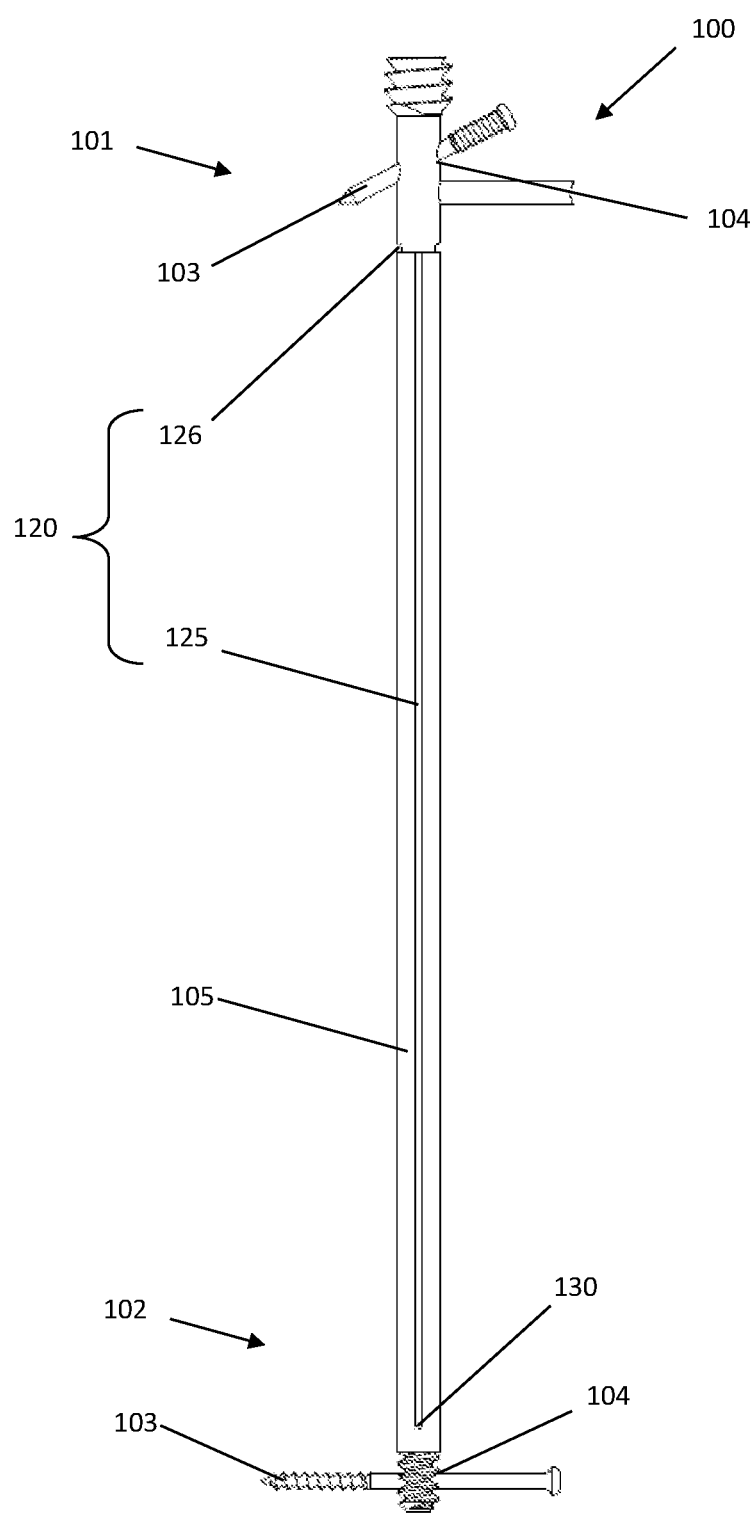
FIG. 2 shows a schematic outside view of the intramedullary nail.

FIG. 2 shows a schematic outside view of the intramedullary nail 100 from FIG. 1. In the top view, one of the lead-throughs 130 from the interior of the intramedullary nail 100 opens out into one of the grooves 125 at the second end 102. The corresponding groove 125 runs axially from the second end 102 to the first end 101 in the outer surface 105 of the intramedullary nail 100, where it is connected in a fluid-conducting manner to the radially circumferential depression 126. A majority of the total length of the intramedullary nail 100 is thus available for an application of an active substance contained in the pharmaceutical fluid over a large area to the surrounding area of the intramedullary nail 100 by means of the fluid-conducting connection of the groves 125 to the outer surface 105.

Figure 3:
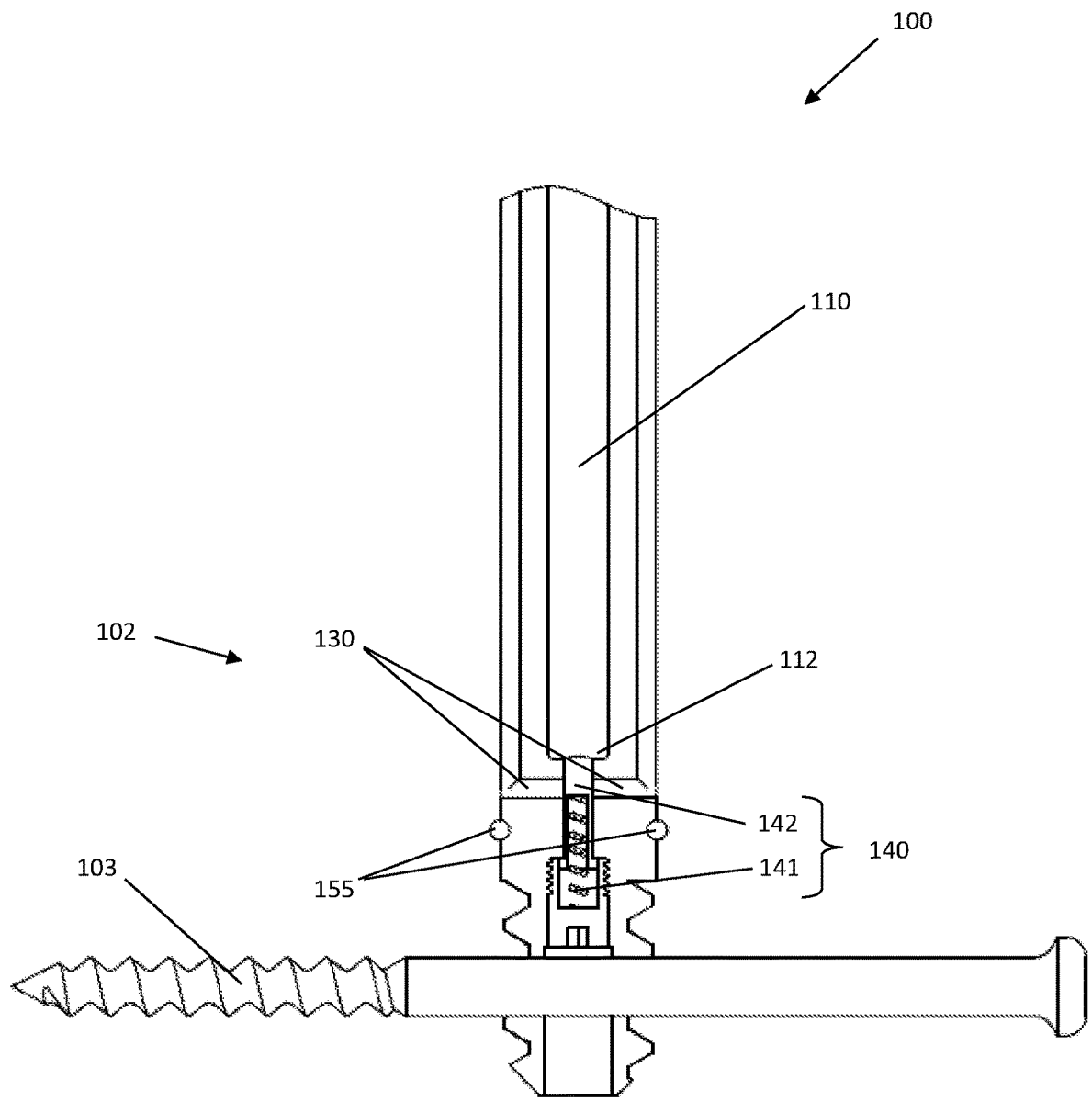
FIG. 3 shows a schematic cross-section of the intramedullary nail comprising a first non-return valve in a closed position.

FIG. 3 shows a section of a schematic cross-section of the intramedullary nail 100 from FIGS. 1 and 2, wherein the first conduit means 110 additionally has a first restoring element 140. The first non-return valve is located at an end 112 of the first conduit means 110 facing the second end 102 of the intramedullary nail 100, directly at the transition to the lead-throughs 130, and is in a closed position. For this purpose, a first restoring element 141 in the form of a spring biases a first piston 142 in such a way that the latter closes the transition from the first conduit means 110 and the lead-throughs 130 in a fluid-conducting manner. In the closed position, a conveying of a pharmaceutical fluid from outside of the intramedullary nail 100 through the lead-throughs 130 into the first conduit means 110 is not possible, so that the risk of a contamination and/or of a clogging of the first conduit means 110 is prevented.

In the shown embodiment, the intramedullary nail 100 has a second sealing ring 155, which radially encompasses the intramedullary nail 100, at the second end 102. After an implantation of the intramedullary nail 100, the second sealing ring 155 cooperates with the bone tissue surrounding the intramedullary nail 100 in such a way that a pharmaceutical fluid, which is conveyed through the intramedullary nail 100 and which escapes out of the lead-throughs 130, is guided in the direction of the first end 101 and not in the direction of the fastening means 103 of the second end 102. An uncontrolled accumulation of the active substance contained in the pharmaceutical fluid in the body of the patient is thus prevented. In a further, non-illustrated embodiment, the intramedullary nail 100 does have the second sealing ring 155, but not the first non-return valve 110.

Figure 4:
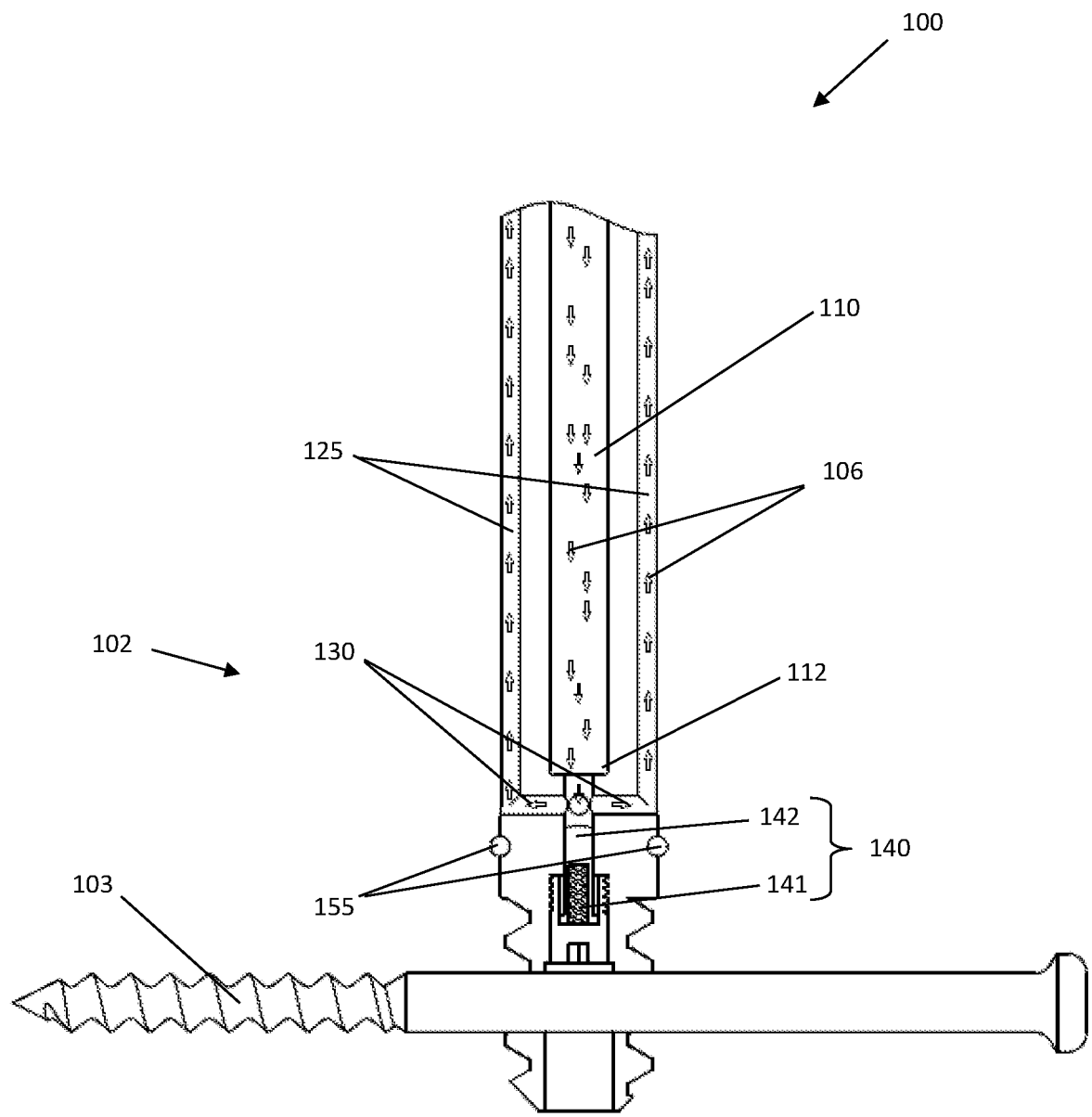
FIG. 4 shows a schematic cross-section of the intramedullary nail comprising the first non-return valve in an open position.

FIG. 4 shows a section of a schematic cross-section of the intramedullary nail 100 from FIGS. 1, 2, and 3, wherein the additional first non-return valve 140 from FIG. 3 is illustrated in an open position. FIG. 4 shows a conveying of a pharmaceutical fluid through the first conduit means 110 in the direction of the lead-throughs 130 and along the grooves 125 back to the first end 101 of the intramedullary nail 100 again, as illustrated by means of the arrows 106. Triggered by a conveying pressure of the pharmaceutical fluid through the first conduit means 110 in the direction of the second end 102, the first non-return valve 140 is in the open position, in that the pharmaceutical fluid displaces the first piston 142 of the first non-return valve 140 against the clamping force of the first restoring element 141 in the direction of the bore 104 at the second end 102. The first non-return valve thus allows a conveying of a pharmaceutical fluid only along the direction of flow illustrated by means of the arrows 106, whereby the risk of a contamination and/or of a clogging of the first conduit means 110 is reduced.

Figure 5:
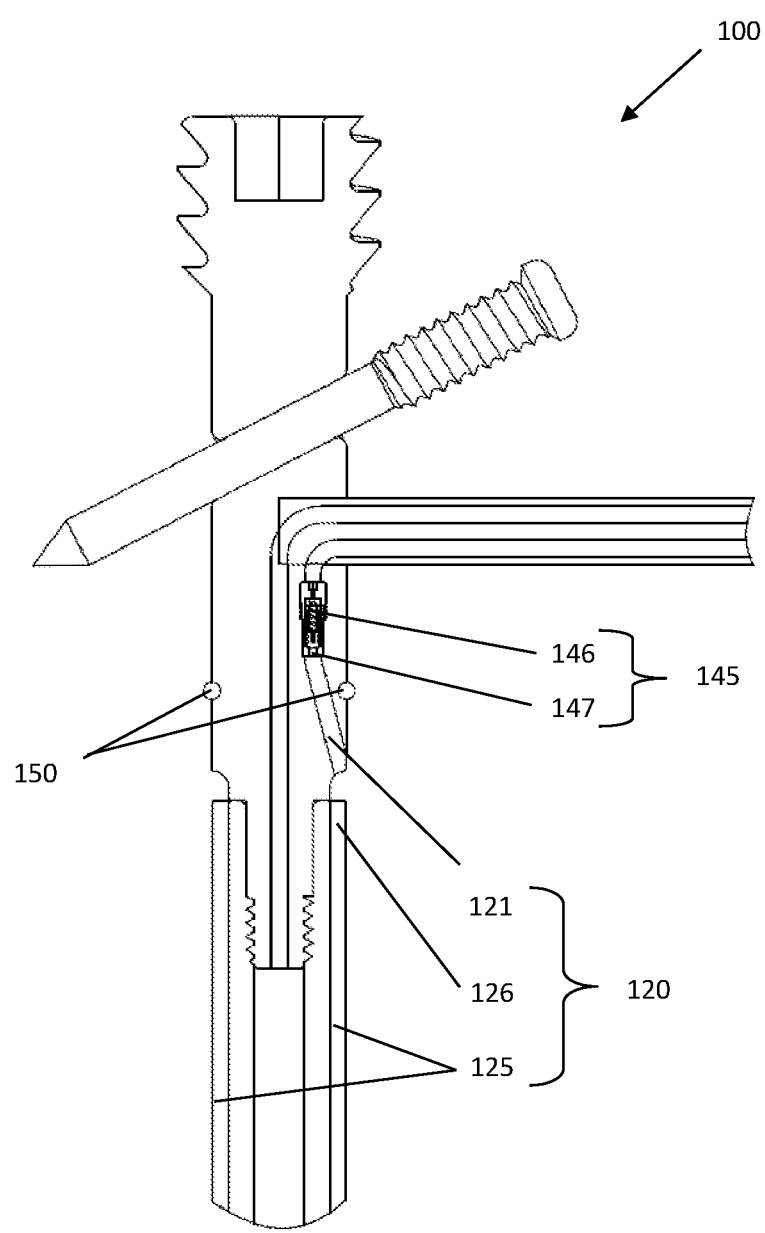
FIG. 5 shows a schematic cross-section of the intramedullary nail comprising a second non-return valve in a closed position.

FIG. 5 shows a section of a schematic cross-section of the intramedullary nail 100 from the preceding figures, wherein the second conduit means 120, in particular the second connector 121, additionally has a second non-return valve 145. FIG. 5 shows the second non-return valve 145 in a closed position. For this purpose, a second restoring element 146 in the form of a spring biases a second piston 147 in such a way that the latter closes the second conduit means 120, in particular the second connector 121, in a fluid-conducting manner in the direction of flow of the radial depression. In the closed position of the second non-return valve 145, a conveying of a pharmaceutical fluid through the second connector 121 in the direction of the second end 102 of the intramedullary nail 100 is not possible.

In a first embodiment, the intramedullary nail 100 only has the second non-return valve 145. In a further, preferred embodiment, the intramedullary nail 100 has the first non-return valve 140 according to FIGS. 3 and 4, and the second non-return valve 145. The second non-return valve 145 is arranged in the canal-like second connector 121, in particular at an end of the second connector 121 facing the radial depression 126.

In the shown embodiment, the intramedullary nail 100 has a first sealing ring 150, which radially encompasses the intramedullary nail 100, at the first end 101. After an implantation of the intramedullary nail 100, the first sealing ring 150 cooperates with the bone tissue surrounding the intramedullary nail 100 in such a way that a pharmaceutical fluid, which is conveyed through the intramedullary nail 100 and which is conveyed through the grooves 125 in the direction of the first end 101, is discharged into the second connector 121, and not in the direction of the fastening means 103 at the first end 101. A controlled accumulation of the active substance contained in the pharmaceutical fluid in the body of the patient is thus prevented. In a further, non-illustrated embodiment, the intramedullary nail 100 does have the second sealing ring 155, but not the first non-return valve 110. In a further embodiment, the intramedullary nail has the first sealing ring 150 as well as the second sealing ring 155. An uncontrolled conveying of a pharmaceutical fluid out of one reservoir into another reservoir, preferably out of the first reservoir into the second reservoir, is thus possible, without resulting in an unwanted accumulation of the active substance contained in the pharmaceutical fluid.

Figure 6:
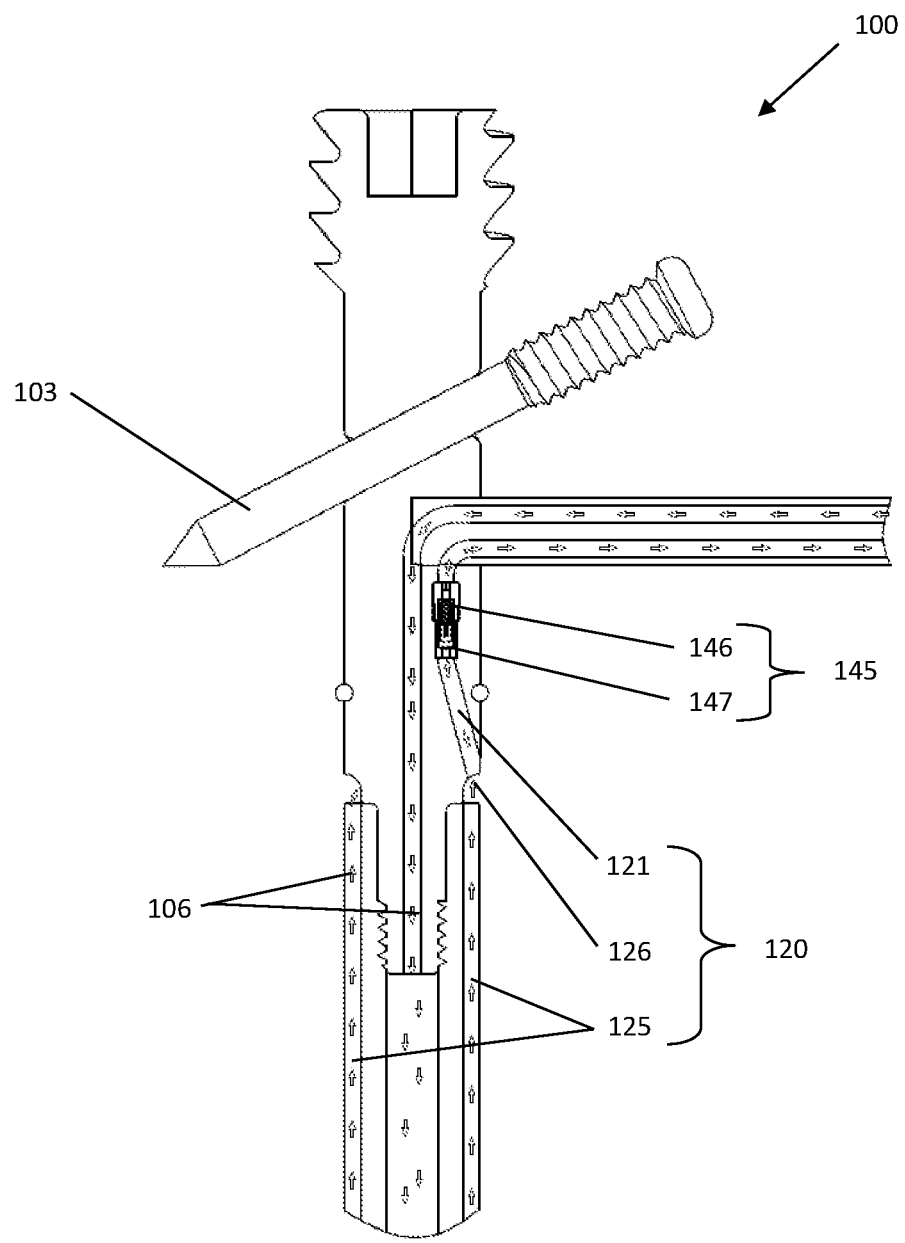
FIG. 6 shows a schematic cross-section of the intramedullary nail comprising the second non-return valve in an open position.

FIG. 6 shows the section of a schematic cross-section of the intramedullary nail 100 from the preceding figures, wherein the additional second non-return valve 145 from FIG. 5 is illustrated in an open position. FIG. 6 shows a conveying of a pharmaceutical fluid through the first conduit means 110 in the direction of the second end 102, and through the second conduit means 120 back in the direction of the first end 101 of the intramedullary nail again, as illustrated by means of the arrows 106. Triggered by a conveying pressure, which is caused by the conveying of the pharmaceutical fluid through the intramedullary nail 100, the second non-return valve 145 is in the open position, in that the pharmaceutical fluid displaces the second piston 147 of the second non-return valve 145 against the clamping force of the second restoring element 146 in the direction of the bore 104 at the first end 101. The second non-return valve thus allows a conveying of a pharmaceutical fluid only along the direction of flow illustrated by means of the arrows 106, whereby the risk of a contamination and/or of a clogging of the first conduit means 110 is reduced.

Figure 7:
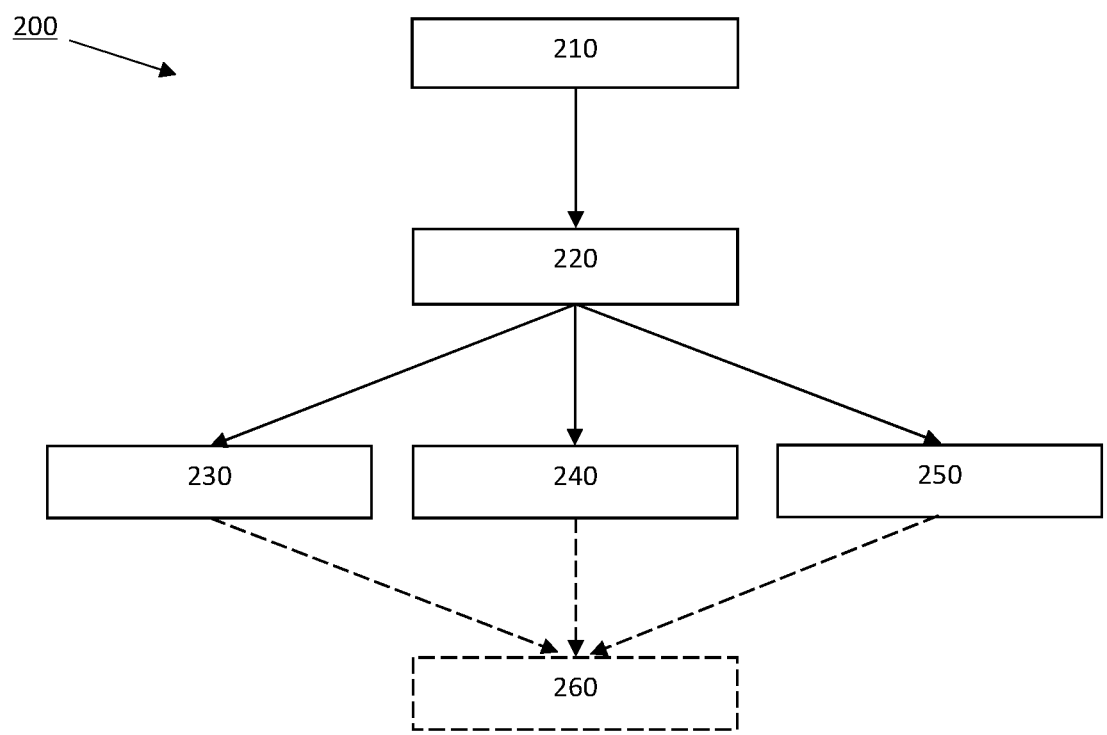
FIG. 7 shows a method for treating a patient by means of an intramedullary nail.

FIG. 7 shows a flowchart of a method 200 for the treatment of bone fractures and for the application of a pharmaceutical fluid in the area of the bone canal by means of an intramedullary nail, comprising steps 210, 220, 230, and/or 240, as well as an optional step 250. In step 210, the intramedullary nail is implanted in the bone canal, and a first conduit means of the intramedullary nail is connected to a first reservoir for pharmaceutical fluids, as well as a second conduit means of the intramedullary nail is connected in a fluid-conducting manner to a second reservoir for pharmaceutical fluids, for example via one or several hoses in step 220. The method 200 can subsequently be performed in three different ways. In a first embodiment of the method 200, a pharmaceutical fluid is at least partially conveyed from the first reservoir into the second reservoir in step 230, for example via pumping. A conveying of the pharmaceutical fluid from the second reservoir into the first reservoir does not take place. In a second embodiment of the method 200, a pharmaceutical fluid is at least partially conveyed from the second reservoir into the first reservoir in step 240 via pumping. A conveying of the pharmaceutical fluid from the first reservoir into the second reservoir does not take place. In the third embodiment of the method 200, an at least partial conveying of a pharmaceutical fluid from the first reservoir into the second reservoir, as well as an at least partial conveying from the second reservoir into the first reservoir is performed in a step 250. The first reservoir and the second reservoir can thereby in each case store the same pharmaceutical fluid or in each case a different pharmaceutical fluid prior to the first conveying, or only the first reservoir or only the second reservoir store a pharmaceutical fluid prior to the first conveying. After finishing the steps 230, 240, or 250, the first reservoir is separated from the first conduit means, and the second reservoir is separated from the second conduit means in a fluid-conducting manner in an optional step 260.

The features disclosed in the claims, the description, and in the figures, can be essential for various embodiments of the claimed invention, both separately and in any combination with one another. The features disclosed for the intramedullary nail are also disclosed for the method, and vice versa.

LIST OF REFERENCE NUMERALS 100 intramedullary nail
101 first end
102 second end
103 fastening means
104 bore
105 outer surface
106 arrows
107 screw connection
110 first conduit means
111 first connector
120 second conduit means
121 second connector
125 groove
126 radial depression
130 lead-through
140 first non-return valve
141 first restoring element
142 first piston
145 second non-return valve
146 second restoring element
147 second piston
150 first sealing ring
155 second sealing ring
200 method for the treatment of bone fractures
210 implantation
220 fluid-conducting connecting
230 conveying from first reservoir into second reservoir
240 conveying from second reservoir into first reservoir
250 conveying from first reservoir into second reservoir and from second reservoir into first reservoir
260 optional fluid-conducting separating'

The invention claimed is:

1. An intramedullary nail for the application of a pharmaceutical fluid, comprising
a fluid-conducting first conduit that extends axially within the intramedullary nail and is connectable to a first reservoir for the pharmaceutical fluid;
a plurality of lead-throughs that connect the first conduit in a fluid-conducting manner to an outer surface of the intramedullary nail; and
a fluid-conducting second conduit that connects the outer surface to a second reservoir and is configured to convey the pharmaceutical fluid between the first reservoir and the second reservoir, wherein the first conduit comprises a first connector for the fluid-conducting connection to the first reservoir, and the second conduit comprises a plurality of axially extending grooves that extend in and axially along the outer surface such that the plurality of grooves extend at least partially along and parallel to a longitudinal axis of the intramedullary nail and a second connector for the fluid-conducting connection to the second reservoir, wherein the first connector and the second connector are arranged at a first end of the intramedullary nail,
wherein the intramedullary nail has the same number of lead-throughs as the plurality of grooves, wherein one groove is in each case interconnected in a fluid conducting manner to a respective lead-through, and the lead-throughs are arranged at a second end of the intramedullary nail opposite to the first end, and
wherein the second conduit is configured and arranged to discharge the pharmaceutical fluid from the outer surface of the intramedullary nail at the first end of the intramedullary nail.

2. The intramedullary nail according to claim 1, wherein each of the plurality of grooves is connected in a fluid-conducting manner to at least one lead-through.

3. The intramedullary nail according to claim 1, wherein the second conduit is formed as two to six extending grooves in the outer surface, and the intramedullary nail has two to six lead-throughs.

4. The intramedullary nail according to claim 1, wherein the first conduit has a first non-return valve.

5. The intramedullary nail according to claim 4, wherein the first non-return valve is fluid-permeable in the direction of the lead-throughs.

6. The intramedullary nail according to claim 4, wherein the first non-return valve has a first restoring element.

7. The intramedullary nail according to claim 1, wherein the second conduit has a second non-return valve.

8. The intramedullary nail according to claim 7, wherein the second non-return valve is embodied so as to be fluid-impermeable in the direction of the outer surface.

9. The intramedullary nail according to claim 7, wherein the second non-return valve has a second restoring element.

10. The intramedullary nail according to claim 1, wherein the intramedullary nail has at least one bore in order to fix the intramedullary nail inside a bone canal.

11. The intramedullary nail according to claim 1, wherein the first conduit, the at least one lead-through, and the second conduit are connected in a fluid-conducting manner such that the first reservoir is connectable to the second reservoir via the first conduit, the at least one lead-through, the outer surface, and the second conduit, wherein the outer surface is configured to be in physical contact with bone tissue of a patient.

12. The intramedullary nail according to claim 1, wherein the at least one lead-through and the second conduit are directly connected to one another and wherein the plurality of grooves are not connected to one another in a fluid-conducting manner.

13. The intramedullary nail according to claim 1, wherein the first conduit and the second conduit extend at least partially parallel to the longitudinal axis of the intramedullary nail and extend longitudinally over between 70 percent to 100 percent of a total length of the intramedullary nail.

14. The intramedullary nail according to claim 1, wherein the second conduit extends axially from the first end to the second end of the intramedullary nail in the outer surface.

15. The intramedullary nail according to claim 1, wherein the first connector and the second connector are arranged at the first end of the intramedullary nail such that supply and discharge of the fluid into and out of a bone canal take place at the same end of a bone.

16. The intramedullary nail according to claim 1, wherein the plurality of grooves are radially distributed over the outer surface and extend longitudinally over between 50 percent to 100 percent of a total length of the intramedullary nail.

17. The intramedullary nail according to claim 16, wherein the plurality of grooves are radially offset from one another at an angle.

18. A method for the treatment of bone fractures and for the application of a pharmaceutical fluid into the area of the bone canal using an intramedullary nail comprising:

a fluid-conducting first conduit, which runs axially in the intramedullary nail and which is connectable to a first reservoir for the pharmaceutical fluid, wherein the first conduit comprises a first connector for the fluid-conducting connection to the first reservoir, a fluid-conducting second conduit comprising a plurality of axially extending grooves that extend in and axially along an outer surface of the intramedullary nail such that the plurality of grooves extend at least partially along and parallel to a longitudinal axis of the intramedullary nail and a second connector for the fluid-conducting connection to a second reservoir, wherein the first connector and the second connector are arranged at a first end of the intramedullary nail, at least one lead-through, which connects the first conduit in a fluid-conducting manner to an outer surface of the intramedullary nail, wherein the outer surface is connectable via the fluid-conducting second conduit, to the second reservoir for the pharmaceutical fluid, wherein the intramedullary nail has the same number of lead-throughs as the plurality of grooves, wherein one groove is in each case interconnected in a fluid conducting manner to a respective lead-through, and the lead-throughs are arranged at a second end of the intramedullary nail opposite to the first end, and wherein the second conduit is configured and arranged to discharge the pharmaceutical fluid from the outer surface of the intramedullary nail at the first end of the intramedullary nail, the method comprising the steps of a) implanting the intramedullary nail into the bone canal;
b) fluid-conducting connection of the first conduit to the first reservoir and of the second conduit to the second reservoir, and at least one of:
c1) at least partial conveying of the pharmaceutical fluid out of the first reservoir via the first conduit, the at least one lead-through, the outer surface, and the second conduit into the second reservoir; and
c2) at least partial conveying of the pharmaceutical fluid out of the second reservoir via the second conduit, the outer surface, the at least one lead-through, and the first conduit into the first reservoir.

19. The method according to claim 18, the method comprising the steps a), b), and c1).

20. The method according to claim 18, wherein the at least one of the at least partial conveying of the pharmaceutical fluid out of the first reservoir and the at least partial conveying of the pharmaceutical fluid out of the second reservoir via the second conduit comprises flowing the pharmaceutical fluid along the longitudinal axis of the intramedullary nail and longitudinally through the first conduit and inside the intramedullary nail in a first direction toward the second end of the intramedullary nail, and longitudinally along the second conduit on the outer surface of the intramedullary nail in a second direction that is opposite the first direction and toward the first end of the intramedullary nail, wherein the fluid comes into contact with bone tissue of the bone via the outer surface of the intramedullary nail.

* * * * *